United States Patent
Schumacher

(10) Patent No.: US 6,548,812 B1
(45) Date of Patent: Apr. 15, 2003

(54) DEVICE FOR DETECTING THE PROPERTIES OF A WEB OF MATERIAL TRANSPORTED IN THE LONGITUDINAL DIRECTION

(75) Inventor: Ursula Schumacher, Jülich (DE)

(73) Assignee: Metso Automation Oy (FI)

( * ) Notice: Subject to any disclaimer, the term of this patent is extended or adjusted under 35 U.S.C. 154(b) by 0 days.

(21) Appl. No.: 09/831,089
(22) PCT Filed: Aug. 12, 1999
(86) PCT No.: PCT/DE99/02530
§ 371 (c)(1),
(2), (4) Date: May 2, 2001
(87) PCT Pub. No.: WO00/26648
PCT Pub. Date: May 11, 2000

(30) Foreign Application Priority Data

Nov. 2, 1998  (DE) .......................... 198 50 335

(51) Int. Cl.$^7$ ........................... G01V 3/36; G01N 21/86
(52) U.S. Cl. ............................ 250/339.02; 250/339.01; 250/358.1; 250/359.1
(58) Field of Search ................ 250/339, 559, 250/358.1, 359.1, 360.1

(56) References Cited

U.S. PATENT DOCUMENTS

| 4,756,619 A | 7/1988 | Gerlinger et al. |
| 5,592,291 A | 1/1997 | Iida |
| 5,724,437 A | * 3/1998 | Bucher et al. ............... 382/112 |

FOREIGN PATENT DOCUMENTS

| DE | 29716331 U1 | 1/1998 |
| DE | 19709963 A1 | 9/1998 |
| DE | 19728966 A1 | 10/1998 |

* cited by examiner

Primary Examiner—Constantine Hannaher
Assistant Examiner—Timothy Moran
(74) Attorney, Agent, or Firm—Akerman Senterfitt

(57) ABSTRACT

A device for detecting properties of a web of material has a crossbar extending across the web of material. An infrared spectrometer having a holographic grating is provided an has an input side and an output side. Infrared detectors are arranged at the output side of the infrared spectrometer and are formed by a detector matrix having n lines and m rows of infrared sensitive individual sensors. A plurality of optical waveguides are provided, each waveguide having an entrance area and an exit area. The entrance area is fastened to said crossbar, located in vicinity of the surface of the web of material and is oriented towards said surface. The exit areas of the optical waveguides are connected to the input side of the infrared spectrometer. The optical waveguides are arranged side by side in one line at this input side, so that infrared spectra inputted into the entrance areas of the individual optical waveguides appear in rows side by side at the output side of the spectrometer, and the spectra of up to m optical waveguides are distributed and detected in up to n spectral areas.

16 Claims, 1 Drawing Sheet

DEVICE FOR DETECTING THE PROPERTIES OF A WEB OF MATERIAL TRANSPORTED IN THE LONGITUDINAL DIRECTION

BACKGROUND OF THE INVENTION

1. Field of the Invention

The invention relates to a device for detecting properties of a web of material conveyed in longitudinal direction, e.g., a web of paper, a) with a plurality of optical waveguides having their entrance areas located each in the vicinity of the surface of the web of material and oriented to said surface and being fastened to a crossbar extending across the web of material, b) with an infrared spectrometer to which input the exit areas of the optical waveguides are connected and c) with infrared detectors at the output of the infrared spectrometer.

2. Description of the Prior Art

Devices and methods of this type are used in online process controlling in the continuous fabrication of sheet materials such as paper, textile, foils, and so on. The device permits to specifically chemically detect most of the processing chemicals. In this way, even the fastest fabrication procedures as they occur, e.g., in paper making and finishing may be monitored with sufficient accuracy. The device is therefor suited for all continuous manufacturing processes in which one or more components determine the quality. For this reason, it is mounted on mixers, calenders, padding machines, doctor blades, steamers and driers in order to be able to more constantly regulate components, additives, applications of products in coating, impregnating, laminating as well as dampness in the course of drying.

The device of the type mentioned above has been previously proposed in DE 197 09 963. In this device, the individual optical waveguides, which are also known as optical fibers and are arranged on the crossbar, are led to a switch that consecutively brings each and every single optical fiber in optical contact with a transfer fibre connected to a spectrometer for a period of time. This procedure is also known as multiplexing. Accordingly, all of the individual fibers are connected one after the other to the spectrometer for a short time period over which the optical signal detected by the corresponding individual optical fiber is interpreted.

This embodiment presents the disadvantage that on one side a mechanically operating device, viz., the switch, is used that has to provide optical contact between different optical fibers with very high accuracy. Practical use compounds the difficulty of durably operating a switch in such a manner that it accurately connects and transmits the optical signals. On the other side, the switch provides little time only to detect the signal of one single optical fiber. This signifies that the optical signal delivered by this fiber is only detected for a very small share of the overall time in time average. This makes it difficult to completely detect a web of material. It is not possible to thus obtain an overall picture of the web of material as it is increasingly demanded.

It is the object of the present invention to develop the device of the type mentioned above in such a manner that a mechanical switch, which is always complicated in manufacturing and in practical operation, is relinquished and that a higher detection rate is achieved.

SUMMARY OF THE INVENTION

Starting from the device of the type mentioned above, the solution to this object is to provide the infrared spectrometer with a holographic grating, to have the optical waveguides arranged side by side in one line at the input of the spectrometer in such a manner that the infrared spectra of the signals of the individual optical waveguides appear in rows side by side at the output of the spectrometer and that the infrared detectors are formed at the output by a detector matrix with n lines and m rows of infrared sensitive individual sensors, the spectra of up to m optical waveguides may be distributed and detected in up to n spectral areas.

This device makes it possible to concurrently monitor m areas of the web of material. The m entrance areas of the optical waveguides are oriented onto these m areas. The number of the entrance areas is preferably less than m, e.g., 0.8 times m, 0.5 times m. Of each and every single area of the web of material observed through the input range, a complete IR spectrum is permanently imaged on the matrix of the detector. It is discretional how this matrix is interpreted, but it is in any case possible to electrically detect and interpret permanently the spectra amounting to a total of up to m spectra.

Accordingly, the device according to the invention provides the possibility to virtually completely sample the web of material to be tested and examined. In other words, it becomes possible to obtain an overall picture of this web of material. As compared to the devices of the art, the detection rate is substantially higher in any event.

The detector matrices used are commercially available arrays as they are particularly utilized in cameras. Detector matrices as they may be used in the invention are offered by the firm Rockwell or by Sensors Unlimited, Inc. for example and are known as focal plane arrays. They are typically designed for the wavelength range of 0.9 to 1.7 micrometers. The number m of rows is adapted to the infrared spectrometer, the individual spectra are to substantially illuminate the individual rows. The number of rows of the detector matrix is usually higher than the number of optical waveguides, in a preferred development, at least one line is always left unused between two spectra in order to achieve a clear separation between neighboring spectra. It is moreover absolutely possible and even intentional to combine and to electrically operate in common several neighboring individual sensors and accordingly pixels. The device according to the invention utilizes detector matrices as they are in fact to be found on the market. With these matrices, the size of the individual sensors is the smallest possible so that high resolution is achieved. This however is not necessary for the device according to the invention.

Owing to the use of a holographic grating, it is possible to precisely devise the grating, the design being accurately calculated for the selected position of input and output of the spectrometer, respectively. In the preferred embodiment, the holographic grating has been given a cylindrical convex shape. In another preferred embodiment, the image of the input is created on the output by way of mirror optics. Therefore, a concave mirror is preferably arranged between input and grating, another concave mirror being preferably provided between the grating and the output.

Ratios of between 0.5 to 1 and 1 to 0.5 proved to be appropriate as an image ratio between input and output of the spectrometer, the image ratio of preference being approximately 1 to 1. Owing to the relatively small areas of the commercially available detector matrices this signifies very small surfaces for the input of the spectrometer which implies the need to use absolutely thin optical fibers at the input. Typically, optical fibers 50 to 60 micrometers in diameter are used. They are packed tightly into the input of the spectrometer, being preferably arranged in line. A zigzag line is also possible.

The use of relatively thin optical waveguides in the range of 50 to 60 micrometers at the input of the spectrometer requires that the same optical waveguides be continued until they reach the entrance area or that thicker optical waveguides, e.g., about 0.5 mm in diameter, be used at the entrance area and to then couple these to the thinner optical waveguides. The way that has been described first presents the advantage that it is not necessary to provide a coupling place between a thick and a thin optical waveguide but has the disadvantage that the extremely thin optical waveguide is very difficult to manipulate. This drawback may be addressed in that the optical waveguides are provided with a relatively thick cladding which simplifies their manipulation. This cladding only is dropped immediately in front of the input of the spectrometer where the optical waveguides are arranged in tight packing side by side. The disadvantage of the second way is that a number of up to n optical waveguides with a larger diameter has to be coupled to a same number of optical fibers with the small diameter. Although this is technically possible, it is complicated. The second way presents the advantage that it is better and easier to work with the relatively thicker optical waveguides. Both ways have comparable light efficiencies. Although the thicker optical waveguides, which are used in the second way, capture and transfer more light in the first place, this achievement is got lost at the transition from the thick to the thin optical waveguides so that in both ways each optical waveguide delivers approximately the same light flux to the spectrometer.

The lighting fixture used for examining the web of material consists as far as possible in point sources of light. Transmission or reflection may be utilized.

The interpretation of the signals of the detector matrix is carried out according to state of the art methods. Reference is made in this connection to WO 97/20429 for example. It relates to a control device for a CCD element.

The sensitivity of the individual sensors of the detector matrix varies. Methods of adjusting the sensitivity and also all the spectral properties of the individual sensors are well known and are employed for the device according to the invention. To compensate different dark tensions, a chopper may be arranged in the light path of all of the individual channels, it is preferably provided in immediate proximity to the input of the infrared spectrometer. Moreover, the detector matrix may be allocated temperature sensors so that the temperature there may be detected. Through temperature, the parameters of the detector matrix may then be compensated in as far as they depend upon the temperature. For this purpose, well-known methods such as FIR or PDS for example are employed. In this connection, reference is made to the two following publications "Standardization of Near-Infrared Spectrometric Instruments, E. Bouveresse et al. Analytical Chemistry, Vol. 68, No. 6, Mar. 15, 1996" and "Transfer of Near-Infrared Multivariate Calibrations without Standards, Thomas B. Blank et al., Analytical Chemistry, Vo. 68, No. 17, Sep. 1, 1996."

BRIEF DESCRIPTION OF THE DRAWINGS

Further advantages and characteristics of the invention will become apparent in the other claims and in the following description of exemplary embodiments that are not limiting the scope of the invention and are explained in more detail with reference to the drawing.

DESCRIPTION OF THE PREFERRED EMBODIMENTS

Figure 1:
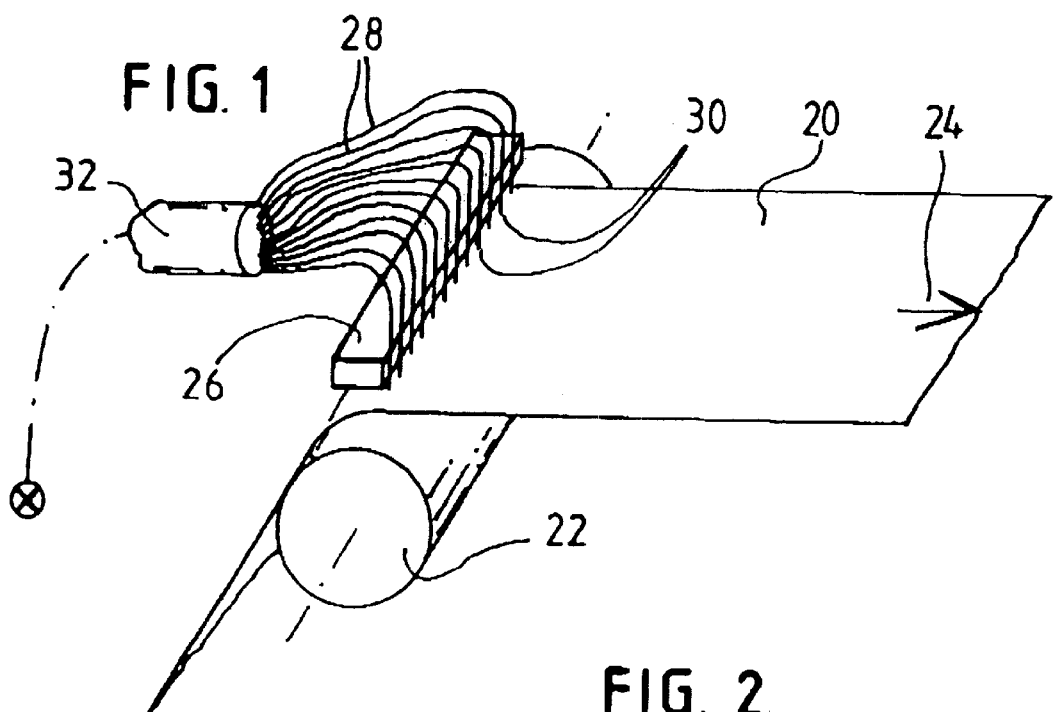
FIG. 1: shows a perspective view of a web of paper conveyed over a roll, said web of paper being allocated a crossbar with optical fibers attached to it.

According to FIG. 1, a web of paper 20 is guided over a roll 22, the machine direction is indicated by arrow 24. A crossbar 26 is fixedly arranged above the roll 22, it has the shape of a beam arranged parallel to the axis of the roll 22. A plurality of optical fibers or optical waveguides 28 is fastened to said crossbar. They each have an entrance area 30 that points downward in FIG. 1, it is oriented to the upper surface of the web of paper 20 and is spaced from said surface by a short distance of 2 mm for example. The various entrance areas 30 are arranged on a line parallel to the axis of the roll 22, they are fastened at regular intervals on the crossbar 26. They are substantially oriented normal to the web of paper 20.

Figure 5:
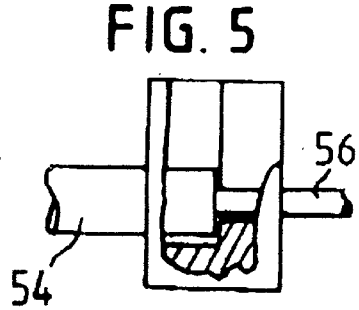
FIG. 5: a partially sectioned side view of a connection region of two optical waveguides having different diameters.

The various optical waveguides 28 are individually guided toward a jacket 32 in which they are combined. In a first embodiment, the optical waveguides 28 have a diameter of approximately 50 to 60 micrometers. In a second embodiment, the optical waveguides have a considerably larger diameter of, e.g., 500 micrometers. They are reduced to optical waveguides of the first mentioned diameter of approximately 50 to 60 micrometers, a device according to FIG. 5 is used for this purpose.

Figure 2:
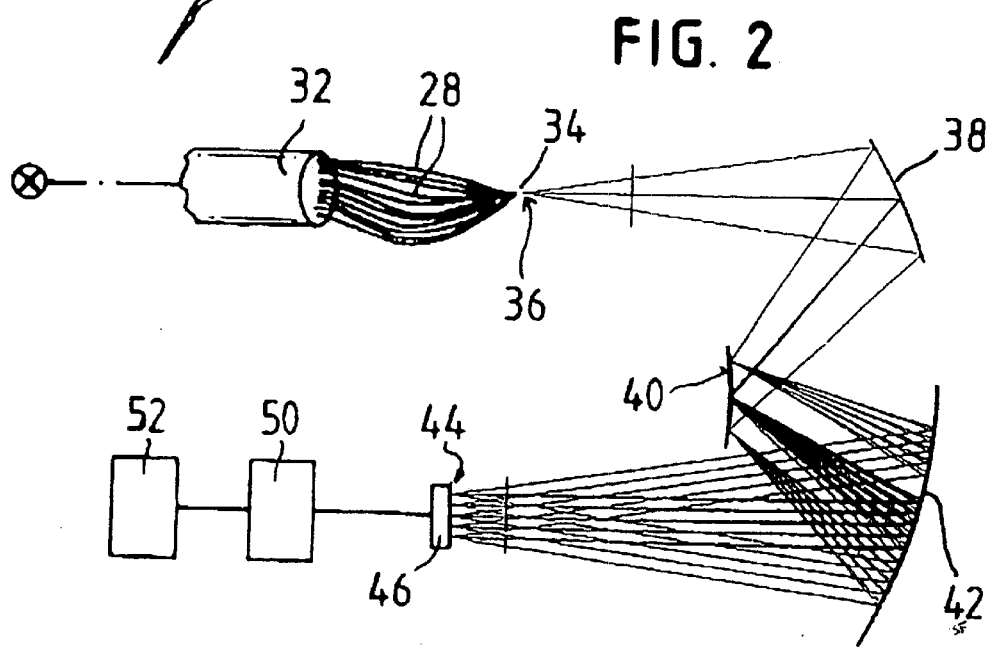
FIG. 2: a basic representation of an infrared spectrometer with an electronic plotting unit.
Figure 4:
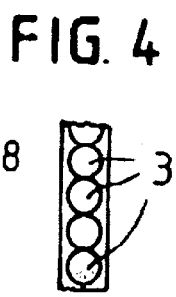
FIG. 4: a front view of part of an exit area of a plurality of optical waveguides

As shown in FIG. 2, the individual optical waveguides 28 exit again the combining jacket 32 one by one and are combined to a line of directly adjacent optical waveguides. FIG. 4 shows a top view of such a line. The arrangement in line of the exit areas 34 of the optical waveguides 28, as it can be visualized as depicted in FIG. 4, is positioned at an input side 36 of a spectrometer. The entrance slot of this spectrometer is virtually realized in this way. The beam path of the light in the spectrometer can be visualized in FIG. 2. The light of the individual optical waveguides 28 exiting the exit areas 34 first falls onto a first concave mirror 38, from there onto a holographic grating 40 formed on a convex cylindrical surface, finally reaches a second concave mirror 42 and is from there imaged on the output side 44 of the spectrometer. The overall ratio of the image realized by the optics described herein above is 1:1.

A detector matrix 46 is arranged at the output 44. The spectrometer is represented in such a manner that the exit areas 34 are lying above each other across the plane of the paper, that is, one looks onto the linear arrangement of the exit areas 34 in longitudinal direction. A spectrum in the wavelength range of 0.9 to 1.7 micrometers is imaged on the detector matrix. The other spectra of the individual light signals of each exit area 34 lie across the plane of the paper below the spectrum represented.

Figure 3:
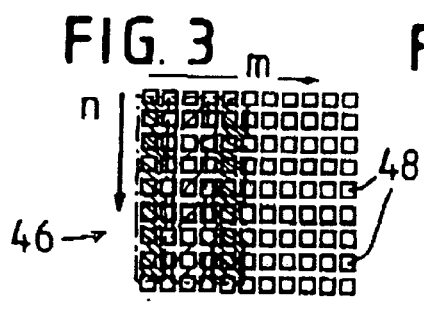
FIG. 3: a top view on a detector matrix.

FIG. 3 shows a view onto the detector matrix 46. For greater ease it has relatively few individual sensors 48, namely a total of ninety-nine individual sensors that are divided into n=nine lines and m=eleven lines. Actually used detector matrices 46 have many times this number of individual sensors, e.g., 128×128 individual sensors.

In the left portion of the detector matrix 46, three spectra are represented side by side for the sake of explanation. The first spectrum substantially illuminates the first row m=1, but in parts also the row m=2. The second spectrum substantially illuminates the third row m=3, but in parts also the two neighboring rows. The same is true for the third spectrum which substantially illuminates the fifth row m=5, but also illuminates the neighboring rows in the process. Only the individual sensors of the first, third and fifth etc. row are utilized for interpretation. It is possible to increase the distance between the rows used. As a result, the spectra of neighboring optical fibers can be readily separated on one side and on the other, specific adjustment of the optics etc. to the effect that the spectra appear side by side in the same sequence on the rows is avoided. Although such an image is not excluded, it involves great difficulties in adjusting and interpreting when small individual sensors as they are found in commercially available focal plane arrays are utilized.

In the example according to FIG. 3, but 50% of the individual sensors 48 are employed. If not all the individual sensors 48 of the detector matrix 46 are interpreted, this signifies greater ease for the topped electronic detecting and plotting unit. Said electronics is represented in FIG. 2. The detector matrix 46 is fitted with a control unit immediately assigned thereto. Via a represented line, this control unit feeds the signals to a plotting station 50 which in turn is connected to a display and storage unit 52 via a line.

The already mentioned FIG. 4 shows a front view of the end of the exit of the optical fiber beam. The single exit areas 34 of each and every optical waveguide 28 may be recognized. The exit areas are oriented along a straight line and are tightly packed side by side without any spacing. The individual exit areas 34 are located in one plane. In the embodiment shown, the end regions of the individual optical waveguides 28 are combined and kept together by means of extrusion.

FIG. 5, which has also been mentioned already, shows how a fiber 54 coming from the left and integral with the entrance area 30 and having a diameter of approximately 0.5 micrometers is optically coupled to a thinner fiber 56 of a diameter of approximately 0.05 micrometers when using the second exemplary embodiment. The structure used has V-shaped indentations that are immediately adjacent to each other. In the representation according to FIG. 5, the view is oriented onto an inner area of such a V-indentation. The indentation is stepped so that, when inserting the fibers 54, 56, they are substantially facing each other in a centrical way. A number of V-indentations of the type mentioned corresponding to the total of up to m optical waveguides are formed in the transmission body as it is shown in FIG. 5. In this way, all the optical waveguides 28 of the second exemplary embodiment described herein above can be reduced to fibers having diameters of approximately 0.06 micrometers.

What is claimed is:

1. A device for detecting properties of a web of material, said web of material having a surface and a longitudinal direction and being conveyed in said longitudinal direction, said device comprising in combination:

a crossbar, said crossbar extending across the web of material;

an infrared spectrometer, said infrared spectrometer having an input side and an output side;

a holographic grating which is arranged in the infrared spectrometer;

infrared detectors, where said infrared detectors are arranged at the output side of the infrared spectrometer and are formed by a detector matrix having n lines and m rows of infrared sensitive individual sensors; and a plurality of optical waveguides, each waveguide having an entrance area and an exit area, said entrance area being located in vicinity of the surface of the web of material, being oriented towards said surface and being fastened to said crossbar, said exit areas of the optical waveguides being connected to the input side, wherein the optical waveguides are arranged side by side in one line at the input side of the spectrometer, infrared spectra inputted into the entrance areas of the individual optical waveguides appearing in rows side by side at the output side of the spectrometer, and the spectra of up to m optical waveguides are distributed and detected in up to n spectral areas.

2. The device according to claim 1, wherein the grating has a cylindrical convex shape.

3. The device according to claim 1, wherein the spectrometer has an image ratio between the input side of the spectrometer and the output side of the spectrometer, and wherein the image ratio ranges from 0.5 to 1 to 1 to 0.5.

4. The device according to claim 3, wherein the image ratio amounts to approximately 1 to 1.

5. The device according to claim 1, wherein the detector matrix is provided with more than 100 rows and with more than 100 lines of infrared sensitive individual sensors.

6. The device according to claim 1, wherein there is always at least one unused row of individual sensors located between two neighboring spectra on the detector matrix.

7. The device according to claim 1, wherein mirror optics is provided that images the input side on the output side.

8. The device according to claim 1, wherein the distance of the entrance areas from the web of material is smaller than 10 mm.

9. The device according to claim 1, wherein the optical waveguides are arranged in a row side by side at regular intervals on a crossbar, and wherein a neighboring waveguide of a certain optical waveguide at the input side of the spectrometer is also a neighboring waveguide of said certain optical waveguide in the arrangement on the crossbar.

10. The device according to claim 1, wherein the web of material is a web of paper.

11. The device according to claim 1, wherein groups of several neighboring individual sensors are groupwise electrically interconnected.

12. The device according to claim 11, wherein groups of four neighboring sensors are electrically interconnected.

13. The device according to claim 1, wherein the distance of the entrance areas from the web of material is smaller than 5 mm.

14. The device according to claim 1, wherein the distance of the entrance areas from the wet of material is smaller than 2 mm.

15. A method for detecting properties of a web of material, said web of material having a surface and a longitudinal direction and being conveyed in said longitudinal direction using a device comprising in combination:

a crossbar, said crossbar extending across the web of material;

an infrared spectrometer, said infrared spectrometer having an input side and an output side;

a holographic grating which is arranged in the infrared spectrometer;

infrared detectors, where said infrared detectors are arranged at the output side of the infrared spectrometer and are formed by a detector matrix having n lines and m rows of infrared sensitive individual sensors; and a plurality of optical waveguides, each waveguide having an entrance area and an exit area, said entrance area being located in vicinity of the surface of the web of material, being oriented towards said surface and being fastened to said crossbar, said exit areas of the optical waveguides being connected to the input side, wherein the optical waveguides are arranged side by side in one line at the input side of the spectrometer, infrared spectra inputted into the entrance areas of the individual optical waveguides appearing in rows side by side at the output side of the spectrometer, and the spectra of up to m optical waveguides are distributed and detected in up to n spectral areas, wherein the detector matrix is interrogated from time to time and at each interrogation only a maximum of 80% of the n×m individual sensors are interrogated.

16. Method according to claim 15, wherein at each interrogation a maximum of 60% of the n×m individual sensors are interrogated.

* * * * *

UNITED STATES PATENT AND TRADEMARK OFFICE
CERTIFICATE OF CORRECTION

PATENT NO. : 6,548,812 B1  
DATED : April 15, 2003  
INVENTOR(S) : Schumacher, Ursula It is certified that error appears in the above-identified patent and that said Letters Patent is hereby corrected as shown below:

Column 6,
Line 51, replace "wet" with -- web --.

Signed and Sealed this

Twentieth Day of April, 2004

JON W. DUDAS
*Acting Director of the United States Patent and Trademark Office*